(12) United States Patent
Rogers et al.

(10) Patent No.: US 6,979,323 B2
(45) Date of Patent: Dec. 27, 2005

(54) CLOSED SYSTEM CATHETERIZATION ASSEMBLY AND RELATED METHODS

(75) Inventors: Bobby E. Rogers, San Diego, CA (US); Mark W. Godfrey, Ramona, CA (US)

(73) Assignee: Aragon Medical Corporation, San Diego, CA (US)

(*) Notice: Subject to any disclaimer, the term of this patent is extended or adjusted under 35 U.S.C. 154(b) by 199 days.

(21) Appl. No.: 10/361,506

(22) Filed: Feb. 7, 2003

(65) Prior Publication Data

US 2004/0158211 A1 Aug. 12, 2004

(51) Int. Cl.[7] ............................................. A61M 25/00
(52) U.S. Cl. .................................... 604/284; 604/523
(58) Field of Search .............................. 604/284, 523, 604/533, 539, 167.02, 167.03, 168.01

(56) References Cited

U.S. PATENT DOCUMENTS

| | | | |
|---|---|---|---|
| 3,680,562 A * | 8/1972 | Wittes et al. ................ 604/500 |
| 3,727,613 A * | 4/1973 | Sorenson et al. ...... 604/165.02 |
| 4,224,943 A * | 9/1980 | Johnson et al. ................ 604/28 |
| 4,311,137 A * | 1/1982 | Gerard ........................... 604/28 |
| 4,559,043 A | 12/1985 | Whitehouse et al. |
| 4,596,557 A * | 6/1986 | Pexa ............................ 604/86 |
| 5,085,645 A | 2/1992 | Purdy et al. |
| 5,108,375 A * | 4/1992 | Harrison et al. ........ 604/167.01 |
| 5,122,123 A | 6/1992 | Vaillancourt |
| 5,167,638 A * | 12/1992 | Felix et al. .................. 604/175 |
| 5,234,410 A | 8/1993 | Graham et al. |
| 5,330,435 A | 7/1994 | Vaillancourt |
| 5,358,490 A * | 10/1994 | Henry et al. ............ 604/467.03 |
| 5,405,323 A | 4/1995 | Rogers et al. |
| 5,417,670 A * | 5/1995 | Bottlik ........................ 604/264 |
| 5,531,701 A | 7/1996 | Luther |
| 5,738,144 A | 4/1998 | Rogers |
| 5,792,104 A * | 8/1998 | Speckman et al. ...... 604/288.02 |
| 5,954,698 A | 9/1999 | Pike |
| 5,967,490 A | 10/1999 | Pike |
| 6,530,911 B1 * | 3/2003 | Utterberg .................... 604/506 |
| 6,610,045 B2 | 8/2003 | Chavez et al. |
| 2002/0120231 A1 * | 8/2002 | Douglas et al. ............... 604/82 |

OTHER PUBLICATIONS

PCT International Search Report in 3 pages.
PCT Written Opinion of the International Searching Authority in 3 pages.

* cited by examiner

Primary Examiner—Sharon Kennedy
(74) Attorney, Agent, or Firm—Knobbe Martens Olson & Bear LLP

(57) ABSTRACT

The invention concerns catheterization assemblies designed to reduce the risk of infection, transmission of bloodborne pathogens, loss of blood, and development of embolisms in a patient. Embodiments of the invention are directed to a catheterization assembly having a catheter hub with multiple access ports. In some embodiments, the catheter hub is permanently attached to a catheter and a valve. The catheter hub provides fluid communication between the valve and the catheter. The catheter hub may also be provided with a sealing member that provides access to a fluid passageway of the catheter hub but which prevents leakage of fluids from the catheter hub. In other embodiments, the catheter hub includes a passageway and an air vent for allowing air to pass out of the catheterization assembly.

42 Claims, 4 Drawing Sheets

CLOSED SYSTEM CATHETERIZATION ASSEMBLY AND RELATED METHODS

BACKGROUND OF THE INVENTION

1. Field of the Invention

The invention relates generally to vascular access devices such as catheter assemblies. The invention is particularly directed to a catheterization assembly designed to reduce the risk of infection, transmission of bloodborne pathogens, loss of blood, and development of embolisms in a patient. The catheterization assembly incorporates a catheter hub that has multiple access ports for allowing air to exit the catheterization assembly, providing fluid communication between a valve and a catheter, and enabling insertion and removal of a catheter introducer without leakage of body fluids from the catheterization assembly.

2. Description of the Related Art

In current medical practice, it is often necessary to have access to the venous system of a patient. For example, it is a common procedure to obtain diagnostic information about the heart or its vessels by inserting a tube (a "catheter") into a vein of the patient and withdrawing blood. Oftentimes, catheterization is necessary to deliver fluids such as medications into the patient's venous system. Additionally, it may be necessary to aspirate fluids from the catheter site to evaluate blood profiles, perform diagnostic assays, etc.

Typically catheterization is conducted by inserting a needle, or other introducer, directly into a patient's vein and pushing or threading a catheter through the entry site created by the needle. Conventional catheterization practice has been to introduce the catheter into the patient's vein and then to attach a secondary component, such as an injection port with a sealed septum, to the catheter to prevent blood leakage, minimize catheter clotting, and to facilitate the introduction of medications or aspirate fluids. In this case the introduction or aspiration of fluids is accomplished by utilizing a needle to penetrate the septum thereby accessing the patient's vasculature via the catheter. The needle is generally inserted into a sealed entry port.

Since the early 1990's, infection by bloodborne pathogens has become a serious concern to health care workers and patients alike. HIV/AIDS and various forms of hepatitis have caused a dramatic shift in the way medical devices are constructed. The elimination of needle sticks and blood contact have been the primary design changes. However, many devices currently marketed as "safety" devices fall short of the goal of preventing the transmission of bloodborne pathogens.

Any device connected to the patient's bloodstream should not have an exposed fluid reservoir due to the potential for bacterial infection from contact with a tainted object. If the fluid reservoir or cavity is not cleaned, then there is a potential for developing bacteria in the fluid reservoir. The bacteria could be introduced into a patient's bloodstream when the device is subsequently used to administer new medications to or aspirate fluids from the patient. Additionally, there is a risk of blood coagulating in the catheter and possibly in the injection apparatus; hence, these components must be frequently replaced thereby creating possible medical complications as well as additional discomfort, pain, and cost to the patient.

Turning in particular to the case of catheters, certain catheters such as Peripherally Inserted Central catheters ("PICCs"), Midline ("Mid") catheters, and Peripheral catheters can remain in a patient for hours or in some cases as long as 180 days. During the course of treatment with a catheter, a patient's venous system may be accessed a number of times to either remove or introduce fluids.

The traditional PICC, Mid, or peripheral catheter is constructed of a length of tubing terminating at the proximal end with a female luer hub (a "catheter hub"). The primary difference between these three catheters is the length of the tubing. The rationale for different lengths is based on the type and duration of the therapy a patient is to receive.

The insertion of these catheters into a patient's venous system can differ procedurally. The peripheral catheter, being the shortest of the three types and measuring about 3.5" in length, is often inserted into a patient's vein through the use of a needle disposed within the catheter tube. These types of catheters are frequently referred to as "over-the-needle catheters." The peripheral catheter is percutaneously inserted into a peripheral vein and terminates in the same peripheral vein. After insertion, the needle is removed, leaving the catheter in the vein. Often, blood will flow out of the back of the luer hub and expose the health care worker to blood contact. Usually, a second component commonly referred to as a "J-loop" is attached to the catheter hub.

A J-loop is a tube approximately 6" in length and is often configured with an injection cap, luer fitting, or needle free valve at its proximal end. Typically, the J-loop is also configured with a male luer fitting at its distal end for attachment to other devices. The J-loop primarily functions to allow handling of injection ports or fluid flow regulating devices away from the point of insertion of the catheter into the patient. Without the use of a J-loop, manipulation of an injection cap, for example, connected directly to the catheter hub would likely result in the inadvertent dislodging of the catheter from the patient. When the J-loop is not supplied with some terminal connector the health care worker must supply one in order to prevent leakage of bodily fluids from the J-loop, or to provide an access port to the catheter via the J-loop.

The PICC and Mid are inserted in a similar fashion. Typically, an introducer is placed into the vein first. The introducer is a thin splittable tube whose internal diameter (ID) is closely matched to the outside diameter (OD) of the internally disposed needle in much the same way as described with reference to the peripheral catheter. Once the introducer has been placed in the vein, the needle is removed and again, blood can be seen to come out of the proximal end of the introducer. The introducer will remain in place and acts as a conduit for threading the PICC or Mid catheter into the patient's vein. Once the PICC or Mid catheter is in the vein, the introducer is removed, and blood can often escape from the hub of the catheter.

Thus, to date, there is an absence of safety devices on the market which reduce or prevent the risk of exposure to bloodborne pathogens to health care workers during and after catheter insertion.

It has also been recognized that known catheterization devices contribute to the incidence of transmission of nosocomial infections to a patient undergoing catheterization. Since 1970, the Center for Disease Control (CDC)'s National Nosocomial Infection Surveillance System (NNIS) has been collecting data on the incidence and etiologies of hospital acquired infections. The majority of hospital-acquired bloodstream infections are associated with the use of a catheter, particularly central venous catheters.

Today, catheter maintenance requires many manipulations of the catheter. For example, every three days, injection caps, valves, and tubing must be replaced. In so doing, the health care worker can inadvertently expose the patient to nosocomial infections caused by bacteria, viruses, and/or fungi. Each and every manipulation that opens the catheter's closed system exposing it to airborne bacteria and touch contamination is a potential source of danger to the patient. Types of organisms that most commonly cause hospital-acquired bloodstream infections include, *Staphylocooccus aureus, Candida* spp., *Escherichia coli, Pseudomonas aeruginosa, Acinetobacter calcoaceticus,* and *Klebsiella pneumoniae*. These microorganisms can infect the patient's bloodstream and, in extreme cases, sepsis and death can result.

The known catheterization devices typically lack features to reduce the risk to the patient of an air embolism. The insertion of a central catheter exposes a patient to the possibility of "sucking" air through the catheter into the patient's bloodstream. This risk can result in death or serious injury to the patient.

Moreover, the known catheterization assemblies often increase the cost of medical care. In today's market, as stated earlier, PICCs can often be in a patient for periods of time up to 180 days. Valves are attached to these catheters to allow for the introduction of drugs, diagnostic agents, etc. Because the valves are detachable, the Center for Disease Control ("CDC") dictates that these valves must be replaced every 72 hours. Valves typically cost approximately $1.50/each (USD). Over a 180 day period, on average, sixty valves must be replaced at a cost of nearly $90.00 (USD). Accordingly, there is a need for catheterization assemblies having valves which prevent blood backflow and which are not required to be replaced periodically to reduce health care costs.

Consequently, there is a constant need in the relevant technology for improved safety devices which prevent or reduce the risk to the patient of transmission of bloodborne pathogens, loss blood, infection, or air embolism in the course of insertion and use of catheter devices. Additionally, affordable safety devices would be a great benefit to both the patient and medical community.

SUMMARY OF THE INVENTION

The catheterization assembly of the invention has several aspects, no single one of which is solely responsible for its desirable attributes. Without limiting the scope of this invention as expressed by the claims which follow, its more prominent features will now be discussed briefly.

To meet the current need for a catheterization assembly that protects health care workers from bloodborne pathogens and needle sticks, in one embodiment the invention provides a fully assembled, safety bloodless catheterization assembly. The catheterization assembly eliminates potential contact with bloodborne pathogens by providing a closed catheterization assembly system. The catheterization assembly also reduces points of connection thereby reducing sources of contamination as well as sources of leaks from separation or loose connections. The catheterization assembly additionally simplifies catheterization by reducing the number of components that a health care worker must attach to a catheterization device in the field.

A feature of the invention is directed to catheter assemblies having a valve integrally attached to a catheter hub. The catheterization assemblies are designed to reduce the risk of infection, transmission of bloodborne pathogens, loss of blood, and development of embolisms in a patient. In some embodiments, a catheterization assembly comprises a valve permanently attached to the hub.

In some embodiments, the catheterization assembly comprises a catheter hub that provides multiple access ports to a catheter inserted in a patient's vein, is configured to allow air to exit the catheter hub, and which provides fluid communication between the catheter and a valve permanently attached to the catheter hub.

One feature of the invention concerns catheterization assembly having a catheter permanently attached to a catheter hub. The hub comprising a first channel having first and second ends, wherein the first channel is configured at the first end to provide fluid communication with the catheter, and wherein the first channel is configured at the second end for permanent attachment to a sealing member. The catheter hub further comprises a second channel having first and second ends, wherein the second channel is configured at the first end to provide fluid communication with the first channel. The catheterization assembly further comprises a first tube having proximal and distal ends, wherein the distal end of the tube is permanently attached to the second end of the second channel. The catheterization assembly further comprises a valve permanently attached to the proximal end of the first tube.

Another aspect of the invention is related to a catheterization assembly comprising a catheter hub permanently attached to a catheter and to a valve, wherein the valve is located outside of the catheter hub.

One embodiment of the invention is directed to a catheter hub. The catheter hub comprises a first passageway having proximal and distal ends, wherein the first passageway is configured at the distal end for non-removable attachment to a catheter, and configured at the proximal end for nonremovable attachment to a sealing member. The catheter hub further comprises a second passageway having proximal and distal ends, wherein the second passageway is configured at the proximal end for non-removable attachment to a valve, and wherein the distal end of the second passageway is configured to provide fluid communication with the first passageway.

Yet another embodiment of the invention relates to a catheter hub for use in catheterization. The hub comprises a first channel providing a fluid passageway through the hub, wherein the first channel is configured to provide fluid communication with a catheter. The hub further comprises a second channel having a proximal end configured to provide fluid communication with the first channel and a distal end configured to provide fluid communication with a valve. The hub further comprises a third channel having a proximal end configured to provide fluid communication with the first channel and a distal end configured to provide fluid communication with an air vent.

Another feature of the invention is directed to a catheterization system. The catheterization system comprises a first tube having a distal end and a proximal end, wherein the first tube defines a fluid passageway between the distal and proximal ends. The catheterization system further comprises a hub attached to the first tube. The hub comprises a first passageway that is colinear with the passageway of the first tube, a second passageway configured to provide fluid communication with the first passageway, and a third passageway configured to provide fluid communication with the first passageway. The catheterization system further comprises a valve in fluid communication with the second passageway and configured to regulate a fluid flow in the second passageway. The catheterization system may further comprise an air vent configured to allow passage of air from the third passageway to the outside of the hub.

Yet another embodiment of the invention concerns a method of manufacturing a catheterization assembly. The method comprises permanently attaching a catheter tube to a catheter hub, and permanently attaching the catheter hub to a valve.

Another feature of the invention concerns a method of manufacturing a catheter assembly. The method comprises permanently attaching a catheter hub to a valve, wherein the catheter hub comprises a catheter tube.

Another aspect of the invention is directed to a catheterization device. The catheterization device comprises means for accessing a patient's vein, and means for supporting the means for accessing, wherein the means for supporting is permanently attached to the means for accessing. The catheterization device further comprises means for regulating a fluid flow in the means for accessing and the means for supporting, wherein the means for regulating is permanently attached to the means for supporting.

BRIEF DESCRIPTION OF THE DRAWINGS

The above and other aspects, features, and advantages of the invention will be better understood by referring to the following detailed description, which should be read in conjunction with the accompanying drawings, in which.

DETAILED DESCRIPTION OF CERTAIN INVENTIVE EMBODIMENTS

Embodiments of the catheterization assemblies and related methods of making and using will now be described with reference to the accompanying figures, wherein like numerals refer to like elements throughout. One embodiment of the invention is directed to a catheterization assembly having a catheter hub that provides multiple access ports to a catheter inserted in a patient's vein, and which is configured to allow air to exit the catheter hub, and which is in fluid communication with a valve attached to the catheter hub. The catheterization assembly is designed to reduce the risk of infection, transmission of bloodborne pathogens, loss of blood, and development of embolisms in a patient.

The terminology used in the description presented herein is not intended to be interpreted in any limited or restrictive manner simply because it is being utilized in conjunction with a detailed description of certain specific embodiments of the invention. Furthermore, embodiments of the invention may include several novel features, no single one of which is solely responsible for its desirable attributes or which is essential to practicing the invention.

Figure 1:
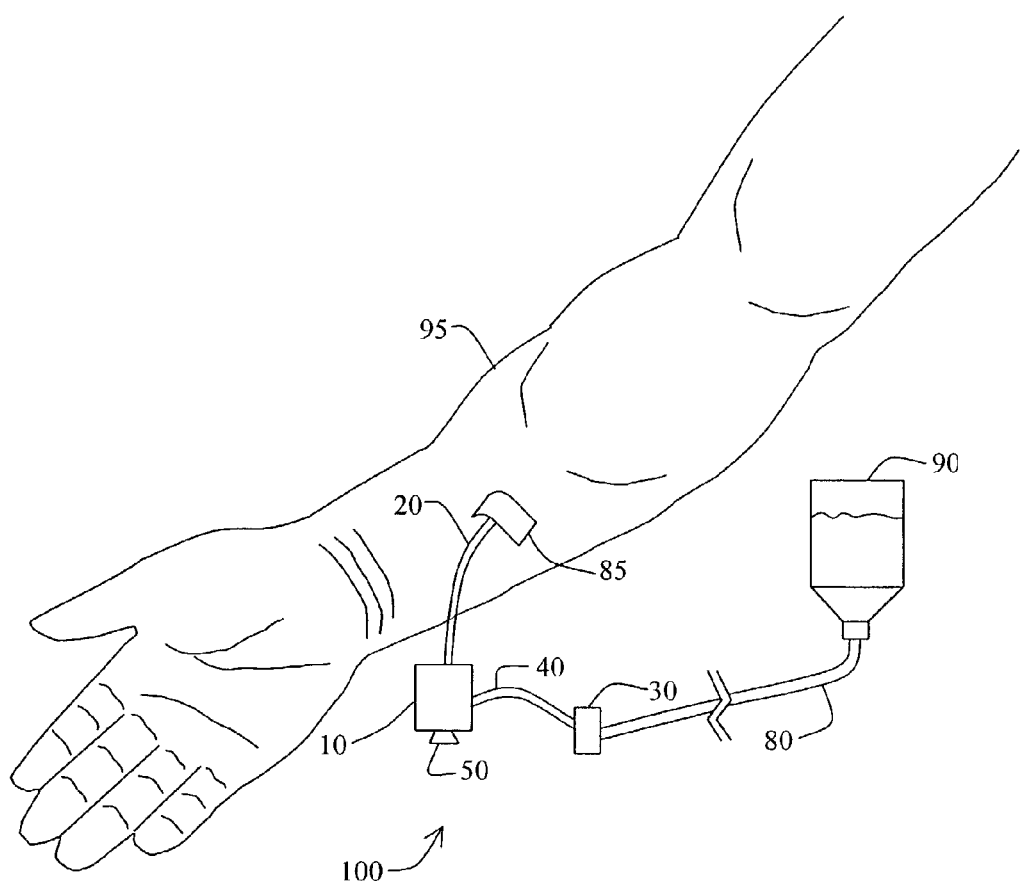
FIG. 1 is a diagram of a catheterization assembly according to the invention as may be used in a clinical setting.

FIG. 1 depicts a catheterization assembly 100 in accordance with the invention as may be used in a clinical setting. The exemplary illustrative use of FIG. 1 is merely by way of a brief introduction, and is not meant to be limiting; moreover, the catheterization assembly 100 will be described in detail with reference to FIGS. 2, 3, and 4 below. In one embodiment, the catheterization assembly 100 comprises a catheter hub 10 having at its proximal end a sealing member 50. The catheter hub 10 is also attached at its distal end to a catheter 20. The catheter hub 10 may be configured to connect permanently to a tube 40, which tube 40 is itself permanently connected or attached to a valve 30. Typically the valve 30 is configured for fluid communication with an intravenous set comprising a tube 80, appropriate fittings (not shown), and a fluid reservoir 90.

In using the catheterization assembly 100, a user inserts the catheter 20 into a vein (not shown) of an arm 95 of patient. The catheter 20 is usually secured to the arm 95 by a piece of tape 85 or other similar device. Once inserted into and secured to the arm 95, the catheter 20 serves to deliver fluids to the patient. For example, fluid from the reservoir 90 flows into the tube 80. The valve 30 regulates flow from the tube 80 to the tube 40 and, of course, to the catheter hub 10. The fluid passes from the catheter hub 10 to the catheter 20 and into the arm 95 of the patient. It should be apparent to the person of ordinary skill in the relevant technology that the catheterization assembly 100 may be used analogously to withdraw blood from the patient. The catheterization assembly 100 is designed so that a user may conveniently fit the patient with the catheterization assembly 100 without blood leaking from the catheter hub 10 and without requiring additional effort in securing other devices to the catheter hub 10.

Figure 2:
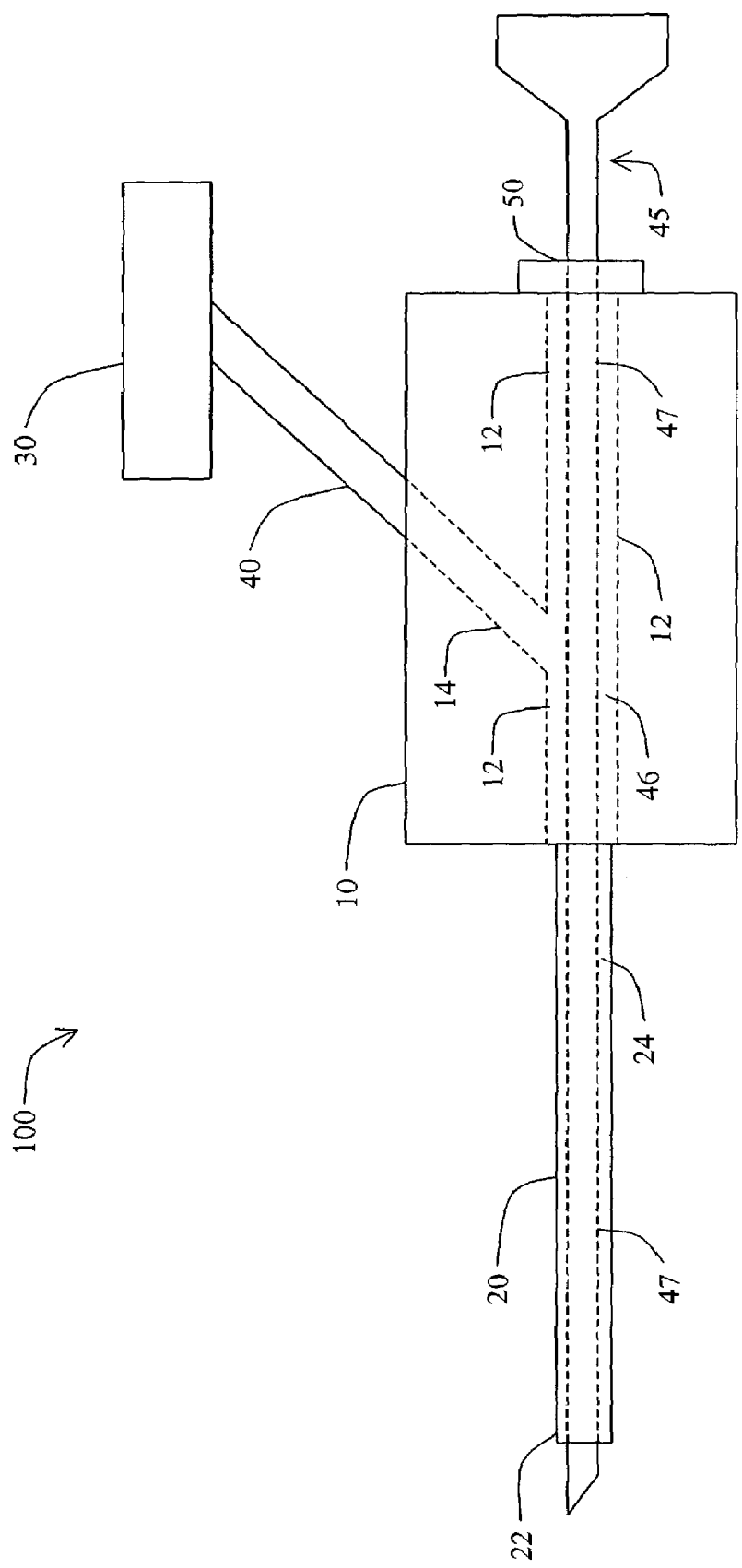
FIG. 2 is schematic illustration of one embodiment of a catheterization assembly according to the invention.

FIG. 2 illustrates one embodiment of a catheterization assembly 100 according to the invention. In this embodiment, a catheterization device 100 comprises a catheter hub 10 attached to a catheter 20. The catheter hub 10 is configured to provide fluid communication between the catheter 20 and a valve 30. In some embodiments, as shown in FIG. 2, a tube 40 provides fluid communication between the catheter hub 10 and the valve 30. In this embodiment, the catheterization device 100 includes a sealing member 50 attached to the catheter hub 10.

The catheter hub 10 comprises a fluid passageway 12 configured so as to provide fluid communication between the catheter hub 10 and a fluid passageway 24 (see FIGS. 3 and 4) of the catheter 20. In one embodiment, the diameter of the fluid passageway 12 is greater than the diameter of a fluid passageway 24 of the catheter 20. The catheter hub 10 also comprises a fluid passageway 14 that is configured so as to provide fluid communication between the fluid passageway 12 and the tube 40 or the valve 30, depending on the specific embodiment. In one embodiment, the sealing member 50 is positioned at the proximal end of the fluid passageway 12 to prevent outflow of fluids from the proximal end of the fluid passageway 12. As is discussed further below, the proximal end of the fluid passageway 12, with its sealing member 50, is configured to provide an access port into the catheter hub 10.

The catheter hub 10 may be a rigid part molded from a plastics such as polycarbonate, ABS, or Acrylic Nylons (e.g., Nylon 6, Nylon 6/6, Nylon 11, Nylon 12). The catheter hub 10 may also be made of a bio-compatible metal such as stainless steel, for example. The methods of manufacturing plastic or metallic catheter hubs are well known in the relevant technology, and a person of ordinary skill in the relevant technology will readily recognize that such methods are applicable to making the catheter hub 10. The fluid passageways 12 and 14 are preferably straight and properly sized for delivering fluids to or aspirating blood from a patient via the catheter 20. The fluid passageways 12 and 14 may be formed by boring holes into a solid piece of plastic or metal, or by plastic molding of the catheter hub 10.

The catheter 20 is preferably constructed from a bio-compatible thermoplastic material such as tubing commercially available from, for example, ExtruMed, Inc. (Placentia, Calif.) or Advanced Polymers (Salem, N.H.). The catheter tube 20 may be coextruded tubing, irradiated high strength balloon tubing, polyolefin heat shrink tubing, single or multi striped tubing, straight or tapered tubing. For example, one of ordinary skill in the relevant technology will appreciate that the catheter 20 may be constructed from any suitable flexible material such as PolyEther Block Amide (PEBAX®) (available from Modified Polymer Components, Inc. of Sunnyvale, Calif.), PolyOlefins (LDPE, LLDPE, HDPE, PP), PolyVinyl Chloride (PVC), PolyVinylidene Fluoride (PVDF), Styrene-Ethylene-Butylene-Styrene Block Copolymer (C-Flex®) (Consolidated Polymer Technologies, Inc., Clearwater, Fla.), and Thermoplastic PolyUrethanes (TPUs). In a preferred embodiment, the catheter 20 is constructed from Thermoplastic PolyUrethanes (TPUs).

The catheter 20 may have length "L" that varies in accordance with the type and duration of the therapy a patient is to receive. In one embodiment, the length of the catheter 20 is preferably about 6" long, more preferably less than about 4.5" long, and most preferably less than about 3.75" long. Of course, the catheterization assembly 100 need not be limited to any one length L. Suitable catheters 20 include, without limitation, Peripherally Inserted Central catheters ("PICCs"), Midline ("Mid") catheters, Peripheral diagnostic and therapeutic catheters. Examples of diagnostic catheters include, without limitation, those catheters used in angiography; advanced sensor catheters for measuring blood oxygen, venous oxygen, and cardiac output; and diagnostic imaging catheters. Examples of therapeutic catheters include, without limitation, atherectomy, angioplasty, RF ablation, etc.

The valve 30 is preferably integrally attached to the tube 40 or to the catheter hub 10. As used here, the phrases "integrally attached" or "permanently attached" are defined to mean "welded, bonded, adhered to, or press fit to in a fixed, non-removable manner." That is, a permanent or integral attachment is designed so that it is not meant to be, and cannot be, disassembled in ordinary use. The tube 40 is preferably also permanently attached to the catheter hub 10.

Since the valve 30 is permanently attached to the catheter hub 10, and the fluid passageway 12 is sealed by the sealing member 50, the catheterization assembly 100 is a closed system. That is, blood or any other biological fluid is prevented from seeping out of the proximal end of catheter hub 10 by the valve 30, as well as the sealing member 50, thereby minimizing the exposure of health care workers to bloodborne pathogens from a patient. Unlike open catheters which allow air to be sucked into the system and pose a risk for developing an embolism, the catheterization assembly 100 includes a permanently attached valve 30 that prevents air from being pulled into the catheter 20 and therefore reduces the incidence of embolism development. Of course, as already stated, in some embodiments the valve 30 may be permanently attached to the catheter hub 10 via the tube 40, as shown in FIG. 2. Because the valve 30 is not detachable, it is not governed by the CDC mandate which dictates that detachable valves must be replaced every 72 hours. Thus, the valve 30 may remain attached to the catheter hub 10 for the duration of the treatment process.

It will be appreciated by one of skill in the relevant technology that the valve 30 may be any needle-free valve assembly, for example, having the foregoing characteristics and which is suitable for integral attachment to the tube 40 or to the catheter hub 10. In some embodiments it is advantageous to have a needle-free valve fixedly attached to a catheterization assembly 100. Such a valve can be used repeatedly without the use of a needle to introduce medications into, or aspirate fluids from, a patient's blood.

In some embodiments, the valve 30 may be a needle-free, positive displacement, luer-activated valve designed to prevent blood from being drawn back into the catheterization assembly 100 at the conclusion of the delivery or aspiration of fluids to or from a patient's venous system. Additionally, valve 30 avoids potential clogging of the catheter hub 10 or catheter 20, while at the same time avoiding potential contamination of the interior of the valve 30 due to contaminants external to the patient that find their way into the interior of the valve 30. The valve 30 is preferably swabbable, thereby preventing the introduction of bacteria into the patient's bloodstream upon subsequent use of the catheterization assembly 100 for dispensing medication.

The materials used for manufacturing the valve 30 preferably have the characteristics of acceptable medical grade plastic that can be precision molded and adapted to maintain its dimensions under normal hospital conditions. When a positive displacement valve 30 is employed, the material of the valve 30 is preferably resistant to alcohol and has a low coefficient of friction. Examples of suitable materials include polycarbonate, PVC, nylon, Delrin, and hydrel. In a preferred embodiment, the valve 30 is constructed from polycarbonate because of its long shelf life, ability to be sterilized, and use in a clear, translucent, or colored form.

As will be apparent to a person of ordinary skill in the relevant technology, a luer fitting (not shown) may be attached to the valve 30. The luer fitting may be, for example, a female luer fitting suitable for connection to T connectors, Y connectors, IV sets or syringes. Advantageously, all of these "IV devices" may have a male luer for mating with the luer fitting of the valve 30.

The tube 40 may be constructed of a molded plastic material. The tube 40 is designed to provide fluid communication between the catheter hub 10 and the valve 30. In some embodiments, the tube 40 may comprise a male fitting that engages a female fitting in the catheter hub 10. However, these fittings must be designed such that once the fitting of the tube 40 is coupled to the fitting of the catheter hub 10 it is not possible to disassemble the connection without utilizing a specialized tool or damaging the catheterization assembly 100. In some embodiments, the tube 40 is configured so as to provide a permanent fluid passageway between the catheter hub 10 and the valve 30. In one embodiment of the catheterization assembly 100, an injection cap (not shown) rather than the valve 30 is permanently attached to the proximal end of the tube 40. Injection caps are well known in the relevant technology.

The sealing member 50 may be a self-sealing septum made from an elastomeric material. The sealing member 50 is preferably permanently attached to the catheter hub 10 at the proximal end of the fluid passageway 12. The sealing member 50 is typically a self-sealing, normally-closed valve that allows introduction of a needle, or other cannula-type device, into the passageway 12. The use and construction of a suitable septum that can perform the functions of the sealing member 50 is well known in the relevant technology, and hence, need not be further described.

As already mentioned, in a preferred embodiment, the catheter 20 is permanently attached to the catheter hub 10. The catheter 20 may be affixed to the catheter hub 10 by any of several means including, for example, chemical bonding, welding, or by a press fit. The fluid passageway 12 provides fluid communication between the catheter 20 and intravenous therapy ("IV") devices external to the catheter hub 10 that may be inserted into, or brought into fluid communication with, the fluid passageway 12 via the sealing member 50. The fluid passageway 12 is also configured to provide fluid communication between the tube 40 and the catheter 20 by being in fluid communication with the fluid passageway 14.

Typically the catheter 20 is made of a soft bio-compatible material that makes it difficult to insert the catheter 20 into a patient because its soft or pliable construction causes the catheter 20 to collapse or bend before entering the patient's veins. In order to quickly and efficiently insert the catheter 20, a flexible stylet, guidewire, or needle is used as a stiffening member inside the catheter 20 during insertion. It is to be understood that the catheterization assemblies described here may be used with any introducer device. However, for convenience, the discussion here will only refer to a needle as the introducer device. Additionally, it will be recognized by the person of ordinary skill in the art that the invention and related methods described here are readily applicable to catheters of rigid construction such as, for example, some well known peripheral catheters.

The needle 4 and the catheterization assembly 100 are preferably pre-assembled by a manufacturer before use in a clinical setting. As assembled, the needle 45 passes through the sealing member 50, fluid passageway 12, and exits the distal end 22 of the catheter 20. The needle 45 is chosen such that the outer surface of its lumen 47 fits close to the internal surface of the catheter 20, thereby substantially preventing fluid flow from the fluid passageway 12 into the fluid passageway 24 of the catheter 20. It should be noted that FIG. 2 shows an exaggerated distance between the lumen 47 and the catheter 20 only to make the drawing clear. However, since the diameter of the fluid passageway 12 is greater than that of the outer diameter of the lumen 47, there is a space 46 around the lumen 47 in the fluid passageway 12 that allows for fluid flow.

Prior to inserting the needle 45 and catheter 20 into a patient, a user may prime the catheterization assembly 100. To accomplish this priming operation, the user attaches a syringe (not shown) to the valve 30 in a conventional manner as is well known in the relevant technology. The syringe is typically pre-filled with a priming fluid such as a heparin or a saline solution. The user introduces the priming fluid from the syringe through the valve 30, the tube 40, and into the fluid passageway 14. From the fluid passageway 14, the priming fluid flows into the fluid passageway 12 and fills the area around the lumen 47 of the needle 45. This priming process aids in removing air from the fluid passageway 12 and the fluid passageway 14, and also aids in cleaning these fluid passageways of blood clots, bacteria, and other contaminants.

After the user primes the catheterization assembly 100, the user may proceed to insert the catheter 20 into a patient in the typical fashion. That is, once the user finds a vein and pierces it with the needle 45 (i.e., the user notices "flashback" in the hub of the needle 45), the user pushes the catheterization assembly 100 toward the vein, thereby inserting the catheter 20 over the needle 45 into the opening created by the needle 45. The user then removes the needle 45 from the catheterization assembly 100. The sealing member 50 prevents blood from flowing out of the proximal end of the catheter hub 10 by self-sealing itself as the user pulls the needle 45 out from the fluid passageway 12 and through the sealing member 50.

It should be apparent to the person of ordinary skill in the relevant technology that with the catheterization assembly 100, removal of the needle 45 from the catheterization assembly 100 does not result in leakage of blood. Additionally, the user need not provide further assemblies, such as a J-loop, fittings, or valves.

In addition to preventing the transmission of blood borne-infections, the invention contemplates methods of reducing the development of air emboli attendant with the placement of a catheterization assembly into the venous system of a patient. In some cases, an open catheterization assembly can allow air to be sucked into the patient, threatening the patient with an air embolism. However, by utilizing a catheterization assembly having a valve attached to a catheter hub to prevent blood backflow, the incidence of air emboli is greatly diminished because the catheterization assembly remains closed.

Figure 3:
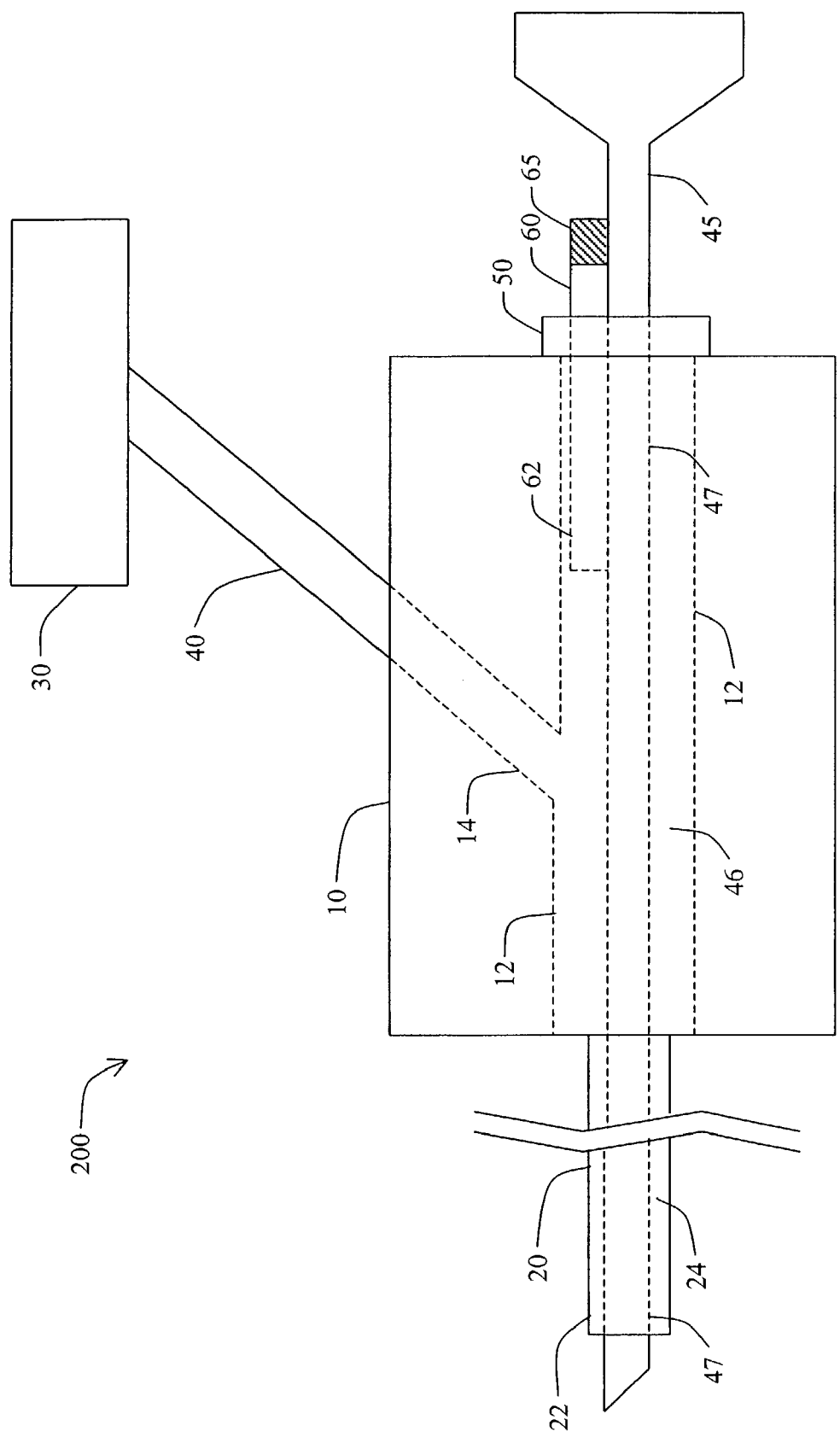
FIG. 3 is a schematic illustration of an exemplary catheterization assembly having an air vent in accordance with one embodiment of the invention.

FIG. 3 illustrates a catheterization assembly 200 similar to the catheterization assembly 100 described above. The catheterization assembly 200 comprises a catheter hub 10 attached to a catheter 20 and a valve 30. The catheter hub 10 may be in fluid communication with the valve 30 via a tube 40 that is attached to both the catheter hub 10 and the valve 30. The catheter hub 10 comprises at least two fluid passageways, namely fluid passageway 12 and fluid passageway 14. The catheterization assembly 200 also includes a sealing member 50 that may be attached to the catheter hub 10 at the proximal end of the fluid passageway 12. The catheter hub 10, catheter 20, valve 30, tube 40, sealing member 50, and fluid passageways are similar in form and construction as those already described with reference to catheterization assembly 100 of FIG. 2.

The catheterization assembly 200, however, additionally comprises a cannula 60 having an air vent 65. In some embodiments, the cannula 60 is attached to the needle 45 so that the cannula 60 and the needle 45 may be inserted into or removed from the fluid passageway 12 simultaneously. In other embodiments, the cannula 60 may be adapted so that a user removes the cannula 60 from the sealing member 50 separately from removal of the needle 45.

The cannula 60 may be a tube made of a bio-medical material, such as stainless steel. The cannula 60 allows flow of air from the fluid passageway 12 into a fluid passageway 62 and out of an air vent 65. The air vent 65 may be an air filter that allows passage of air from the fluid passageway 65 and out of the catheter hub 10. A suitable air vent 65 for use with the catheterization assembly 200 may be constructed from a variety of hydrophobic membranes and filters, including but not limited to Pall Specialty Materials: Emflon PTFE Membranes; Hydrolon Nylon 6,6 Membrane; Supor R Membrane; Pallflex 8E Medium; Pallflex 70 Medium; Pallflex 40 Medium; Pallflex TV2 Medium; Pallflex TX4 Medium; and Pallflex TS6 Medium.

In this embodiment, when the user primes the catheterization assembly 200, the user first introduces a priming fluid into the catheter hub 10 as described above. The priming fluid in this embodiment flows through the valve 30, tube 40, fluid passageway 14, fluid passageway 12, fills the area around the needle 45, and enters the fluid passageway 62. As the priming fluid fills the fluid passageways present in the catheter hub 10, the air vent 65 allows the air in the catheter hub 10 to vent out. When the priming fluid enters the fluid passageway 62, it eventually comes into contact with, and thereby seals, the air vent 65. Hence, an ordinary technician in the relevant technology will appreciate that the air vent 65 is configured to allow passage of air but not of fluids out of the catheter hub 10.

The cannula 60 preferably remains in place until the catheterization assembly 200 is inserted into the patient's vascular system. The person of ordinary skill in the relevant technology will appreciate that in this embodiment the cannula 60 with its vent 65 may be removed safely in a single motion with the removal of needle 45.

Figure 4:
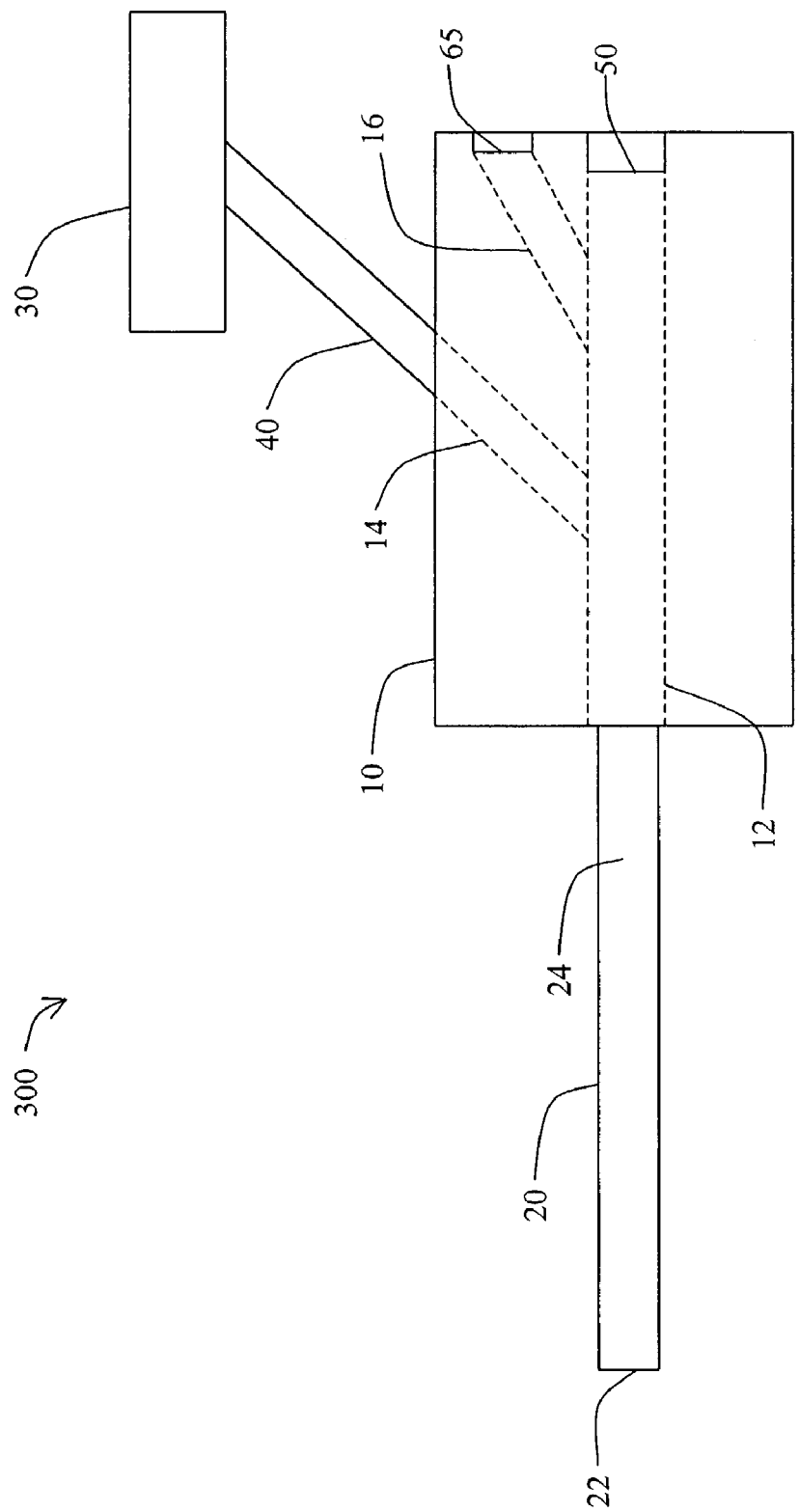
FIG. 4 is a schematic illustration of yet another embodiment of the invention, showing a catheterization assembly having an air vent.

FIG. 4 illustrates schematically a catheterization assembly 300 in accordance with another embodiment of the invention. The catheterization assembly 300 comprises a catheter hub 10 that is in fluid communication with a catheter 20 and a valve 30. In some embodiments, a tube 40 provides a fluid passageway for fluid communication between the catheter hub 10 and the valve 30. Additionally, in some embodiments of the catheterization assembly 300, the catheter hub 10 is preferably permanently attached to the valve 30 and the catheter 20. The catheterization assembly 300 may also include a sealing member 50 that acts as a normally-closed, self-sealing valve that prevents passage of fluid from the fluid passageway 12 out of the catheter hub 10. The sealing member 50 is preferably, but not necessarily, also permanently attached to the catheter hub 10 at the proximal end of the fluid passageway 12. The catheter hub 10, catheter 20, valve 30, tube 40, sealing member 50, and fluid passageways 12 and 14 are of similar form and construction as those described above with reference to catheterization assembly 100.

As shown in FIG. 4, the catheterization assembly 300 may also comprise a catheter hub 10 having a fluid passageway 16 that is fluid communication with the fluid passageway 12. The fluid passageway 16 terminates at an air vent 65, which performs the same function as air vent 65 of FIG. 3, namely air vent 65 permits passage of air out of the catheter hub 10 but does not allow entry or exit of other substances into or out of the catheter hub 10.

Similarly to catheterization assembly 200, when the user primes the catheterization assembly 300, the user first introduces a priming fluid into the catheter hub 10 as described above. The priming fluid in this embodiment flows through the valve 30, tube 40, fluid passageway 14, fluid passageway 12, fills the area around the needle 45, and enters the fluid passageway 16. As the priming fluid fills the fluid passageways present in the catheter hub 10, the air vent 65 allows the air in the catheter hub 10 to vent out. When the priming fluid enters the fluid passageway 16, it eventually comes into contact with, and thereby seals, the air vent 65. The catheter hub 10 is, thus, configured with an integral fluid passageway 16 that allows passage of air out of the catheter hub 10 before insertion of the catheter 20 into a patient's vein.

Another feature of the invention is a method of manufacturing a catheterization assembly, e.g., catheterization assembly 100 of FIG. 2, having a valve 30 fixedly attached to a catheter hub 10. The method comprises permanently attaching a catheter 20 at the distal end of a catheter hub 10. In some embodiments, the catheter 20 is welded to the catheter hub 10; in other embodiments, the catheter 20 is bonded chemically to the catheter hub 10. The method further comprises welding or chemically bonding a valve 30 directly to the catheter hub 10. In some embodiments, a tube 40 or other fluid carrier having suitable end connections, is welded or chemically bonded to the catheter hub 10 at one end and to the valve 30 at the other end. Moreover, in some embodiments a sealing member 50 is permanently welded, chemically bonded, or press fit to the catheter hub 10 at the proximal end of the fluid passageway 12. An ordinary technician will recognize that these permanent attachments may be accomplished by bonding, gluing, ultrasonically welding, or even by providing compression fits. Any manner of providing an attachment that is not meant to be disassembled in normal use is suitable for the purposes of the invention.

Another aspect of the invention concerns a method that facilitates delivering or aspirating fluid to or from a patient. This method employs a catheterization assembly as describe above. The method includes introducing into a vein of a patient a catheter 20 that is permanently attached to a catheter hub 10, which catheter hub 10 is itself permanently attached to a valve 30. A user may employ an introducer, such as needle 45, to create an entry into the vein of a patient for the catheter 20. The user may pass the introducer through the catheter hub 10, into the catheter 20, and pierce the patient's vein. After the user places the catheter 20 in the patient's vein, the user pulls the introducer out of the catheter hub 10, through a sealing member 50, without any fluids exiting the catheter hub 10. After the catheterization assembly 100 is in place, the user may deliver to and/or remove fluids from a patient via the valve 30. Hence, the user employs a catheterization assembly having a catheter hub 10 with multiple ports for delivering or retrieving fluids from a patient. Moreover, as should be apparent to a person of ordinary skill in the art, the catheterization assemblies described do not require the health care worker to separately provide and attach other components to a catheter and its hub during catheterization because the catheterization assemblies of the invention are pre-assembled with the components (e.g., tube 40 and valve 30) typically used in catheterization.

It will be apparent to a person of ordinary skill that the catheterization assemblies and methods described here reduce the transmission of bloodborne infections from patients to health care workers. When using known catheterization devices, blood often seeps out from the catheterization device. By permanently and integrally attaching a valve to a catheter hub at one port of the catheter hub, and by providing a sealing member at a different port of the catheter hub that is for insertion of a catheter introducer (e.g., a needle), fluids are blocked from exiting the catheterization assembly. Accordingly, the health care worker employing the catheterization assembly of the invention is protected from exposure to patient blood and other fluids. Additionally, because the catheterization assemblies of the invention may include needle-free valves, when fluid such as medication is delivered through the needle-free valve or when fluid is aspirated from the needle-free valve, the health care worker is not exposed to needles or the dangers posed by needle sticks. Thus, the risk of transmission of bloodborne pathogens such as HIV, various strains of hepatitis, etc. is reduced or eliminated.

While the above detailed description has shown, described, and pointed out novel features of the catheterization assembly and related methods as applied to various embodiments, it will be understood that various omissions, substitutions, and changes in the form and details of the device or processes illustrated may be made by those skilled in the art without departing from the spirit of the invention. The scope of the invention is indicated by the appended claims rather than by the foregoing description. All changes which come within the meaning and range of equivalency of the claims are to be embraced within their scope.

What is claimed is:

1. A catheterization assembly comprising:
    a catheter;
    a catheter hub permanently attached to the catheter, the hub comprising:
        a first channel having first and second ends, wherein the first channel is configured at the first end to provide fluid communication with the catheter, and wherein the first channel is configured at the second end for permanent attachment to a sealing member; and a second channel having first and second ends, wherein the second channel is configured at the first end to provide fluid communication with the first channel;

a first tube having proximal and distal ends, wherein the distal end of the tube is permanently attached to the second end of the second channel;

a second tube having proximal and distal ends, wherein the distal end of the second tube is configured to provide fluid communication with the first channel, and wherein the proximal end of the second tube comprises an air vent; and a valve permanently attached to the proximal end of the first tube.

2. A catheterization assembly comprising:

a catheter;

a catheter hub permanently attached to the catheter, the hub comprising:

a first channel having first and second ends, wherein the first channel is configured at the first end to provide fluid communication with the catheter, and wherein the first channel is configured at the second end for permanent attachment to a sealing member; and a second channel having first and second ends, wherein the second channel is configured at the first end to provide fluid communication with the first channel;

wherein the hub further comprises a third channel having distal and proximal ends, wherein the third channel is configured at the distal end to provide fluid communication with the first channel, and wherein proximal end of the third channel comprises an air vent; and a first tube having proximal and distal ends, wherein the distal end of the tube is permanently attached to the second end of the second channel; and a valve permanently attached to the proximal end of the first tube.

3. A catheterization assembly comprising:

a catheter;

a catheter hub permanently attached to the catheter; and a valve permanently attached to the hub, wherein the valve is located outside of the hub, and wherein the hub comprises an air vent.

4. The catheterization assembly of claim 3, further comprising a connecting tube configured to provide fluid communication between the hub and the valve, and wherein the connecting tube is permanently attached to the hub and to the valve.

5. The catheterization assembly of claim 4, wherein the hub comprises a sealing member.

6. The catheter assembly of claim 3, wherein the catheter is less than about 4 inches in length.

7. The catheterization assembly according to claim 3, wherein the hub comprises:

a first channel having proximal and distal ends, wherein the first channel is configured at the distal end to connect to the catheter so as to provide fluid communication with the catheter, and wherein the proximal end of the first channel comprises a sealing member;

a second channel having proximal and distal ends, wherein the second channel is configured at the distal end to connect to the first channel so as to provide fluid communication with the first channel, and wherein the second channel is configured at the proximal end to provide fluid communication with the valve.

8. A catheterization assembly comprising:

a catheter;

a catheter hub permanently attached to the catheter, the hub comprising a first channel having proximal and distal ends, wherein the first channel is configured at the distal end to connect to the catheter so as to provide fluid communication with the catheter, and wherein the proximal end of the first channel comprises a sealing member;

a second channel having proximal and distal ends, wherein the second channel is configured at the distal end to connect to the first channel so as to provide fluid communication with the first channel, and wherein the second channel is configured at the proximal end to provide fluid communication with the valve;

a third channel having proximal and distal ends, wherein the third channel is configured at the distal end to provide fluid communication with the first channel, and wherein the proximal end of the third channel comprises an air vent; and a valve permanently attached to the hub, wherein the valve is located outside of the hub.

9. A catheter hub comprising:

a sealing member;

a first passageway in the hub, the first passageway having proximal and distal ends, wherein the first passageway is configured at the distal end for nonremovable attachment to a catheter, and configured at the proximal end for non-removable attachment to the sealing member;

a second passageway in the hub, the second passageway having proximal and distal ends, wherein the second passageway is configured at the proximal end for non-removable attachment to a valve, and wherein the distal end of the second passageway is configured to provide fluid communication with the first passageway, and an air vent in fluid communication with the first passageway and the second passageway, wherein the air vent is configured to allow the passage of air out of the catheter hub.

10. The hub of claim 9, further comprising a valve non-removably attached to the proximal end of the second passageway.

11. The hub of claim 10, wherein the sealing member is a self-sealing septum.

12. A catheter hub for use in catheterization, the hub comprising:

a first channel providing a fluid passageway through the hub, wherein the first channel is configured to provide fluid communication with a catheter;

a second channel having a proximal end configured to provide fluid communication with the first channel and a distal end configured to provide fluid communication with a valve; and a third channel having a proximal end configured to provide fluid communication with the first channel and a distal end configured to provide fluid communication with an air vent.

13. The catheter hub of claim 12, wherein the second channel is non-removably attached to a connecting tube that is configured to provide fluid communication between the second channel and the valve.

14. The catheter hub of claim 13, wherein the connecting tube is non-removably attached to the valve.

15. A catheterization system comprising:

a first tube having a distal end and a proximal end, wherein the first tube defines a fluid passageway between the distal and proximal ends;

a catheter hub attached to the first tube, the hub comprising:
a first passageway that is substantially colinear with the passageway of the first tube in the vicinity of the attachment of the first passageway to the first tube;
a second passageway configured to provide fluid communication with the first passageway; and
a third passageway configured to provide fluid communication with the first passageway;
a valve in fluid communication with the second passageway and configured to regulate a fluid flow in the second passageway; and
an air vent configured to allow passage of air from the third passageway to the outside of the hub.

16. A catheterization system comprising:
a catheter;
a hub attached to the catheter, wherein the hub comprises:
a first fluid passageway that is configured to provide fluid communication with a valve, and wherein the hub comprises a channel having a distal end and a proximal end;
an air vent located at the proximal end of the channel; and
wherein the distal end of the channel is configured to provide fluid communication with the catheter.

17. A catheter hub for a catheterization system, the hub comprising:
a first channel having a proximal end and a distal end, wherein the distal end is configured for fluid communication with a catheter;
a sealing member attached to the proximal end of the first channel;
a second channel having a proximal end and a distal end, wherein the distal end is configured to provide fluid communication with the first channel, and wherein the proximal end is configured to provide fluid communication with a valve, and
an air vent in fluid communication with the first channel, wherein the air vent is configured to allow the passage of air out of the catheter hub.

18. The catheter hub of claim 17, further comprising a tube that is configured to provide fluid communication between the hub and the valve.

19. The catheter hub of claim 18, wherein the tube is permanently attached to the hub and to the valve.

20. The catheter hub of claim 17, further comprising a cannula in fluid communication with the first channel, wherein the cannula passes through the sealing member and into the first channel, and wherein the air vent is attached to end of the cannula.

21. A method of manufacturing a catheter, the method comprising:
permanently attaching a catheter tube to a catheter hub;
permanently attaching a sealing member to the catheter hub;
disposing a cannula comprising an air vent on the catheter hub through the sealing member; and
permanently attaching the catheter hub to a valve.

22. The method of claim 21, wherein permanently attaching a catheter tube comprises permanently attaching a peripheral catheter.

23. The method of claim 22, wherein permanently attaching a peripheral catheter comprises attaching a catheter tube that is less than about 6" long.

24. The method of claim 21, wherein permanently attaching the catheter hub to the valve comprises permanently attaching a tube to both the hub and the valve, wherein the tube is configured to provide fluid communication between the valve and the hub.

25. A method of manufacturing a catheter assembly, the method comprising:
permanently attaching a catheter hub to a valve, wherein the catheter hub comprises a catheter tube and an air vent.

26. The method of claim 25, wherein permanently attaching a catheter hub to a valve comprises attaching a tube to the hub and to the valve, wherein a distal end of the tube is permanently attached to the hub and the proximal end of the tube is permanently attached to the valve, and wherein the tube provides fluid communication between the valve and the hub.

27. The method of claim 25, wherein the catheter tube is a peripheral catheter that is less than about 4" long.

28. A catheterization device comprising:
means for accessing a patient's vein;
means for supporting the means for accessing, wherein the means for supporting is permanently attached to the means for accessing;
means for regulating a fluid flow in the means for accessing and the means for supporting, wherein the means for regulating is permanently attached to the means for supporting; and
means for venting air from the fluid flow.

29. The catheterization device of claim 28, wherein the means for accessing comprises a lumen less than about 4 inches in length.

30. The catheter hub of claim 17, wherein the air vent is further configured to not allow entry or exit of other substances into or out of the catheter hub.

31. The catheter hub of claim 17, wherein the air vent is further configured to not allow the passage of fluids out of the catheter hub.

32. The catheter hub of claim 17, wherein the air vent is further configured to seal if contacted with a fluid from the catheter hub.

33. The method of claim 21, wherein the air vent is configured to allow the passage of air and not allow entry or exit of other substances into or out of the catheter hub.

34. The catheter hub of claim 21, wherein the air vent is configured to not allow the passage of fluids out of the catheter hub.

35. The catheter hub of claim 21, wherein the air vent is further configured to seal if contacted with a fluid from the catheter hub.

36. The method of claim 25, wherein the air vent is configured to allow the passage of air and not allow entry or exit of other substances into or out of the catheter hub.

37. The catheter hub of claim 25, wherein the air vent is configured to not allow the passage of fluids out of the catheter hub.

38. The catheter hub of claim 25, wherein the air vent is further configured to seal if contacted with a fluid from the catheter hub.

39. The method of claim 28, wherein the means for venting air from the fluid flow is configured to allow the passage of air and not allow entry or exit of other substances into or out of the catheterization device.

40. The catheter hub of claim 28, wherein the means for venting air from the fluid flow is configured to not allow the passage of fluids out of the catheterization device.

41. The catheter hub of claim 28, wherein the means for venting air from the fluid flow is configured to seal if contacted with a fluid from the catheterization device.

42. The catheter hub of claim 17, further comprising a cannula in fluid communication with the first channel, the cannula comprising a cannula housing, and wherein the air vent is attached to the cannula housing.

* * * * *